(12) United States Patent
Hölscher et al.

(10) Patent No.: US 8,999,913 B2
(45) Date of Patent: Apr. 7, 2015

(54) FRAGRANCE MIXTURES CONTAINING CYCLOPENT-2-ENYL ETHYL ACETATE

(71) Applicant: Symrise AG, Holzminden (DE)

(72) Inventors: Bernd Hölscher, Halle (DE); Annabel Chmelnyk, Holzminden (DE)

(73) Assignee: Symrise AG, Holzminden (DE)

( * ) Notice: Subject to any disclaimer, the term of this patent is extended or adjusted under 35 U.S.C. 154(b) by 174 days.

(21) Appl. No.: 13/713,516

(22) Filed: Dec. 13, 2012

(65) Prior Publication Data

US 2013/0172429 A1   Jul. 4, 2013

Related U.S. Application Data

(60) Provisional application No. 61/570,632, filed on Dec. 14, 2011.

(30) Foreign Application Priority Data

Dec. 14, 2011  (EP) .................................. 11193578

(51) Int. Cl.

| | |
|---|---|
| *C11B 9/00* | (2006.01) |
| *A61K 8/37* | (2006.01) |
| *A61Q 13/00* | (2006.01) |
| *C11D 3/20* | (2006.01) |
| *C11D 3/50* | (2006.01) |
| *A61K 8/33* | (2006.01) |
| *A61K 8/34* | (2006.01) |
| *A61K 8/35* | (2006.01) |
| *A61Q 5/02* | (2006.01) |
| *A61Q 19/10* | (2006.01) |

(52) U.S. Cl.
CPC . *C11B 9/003* (2013.01); *A61K 8/37* (2013.01); *A61Q 13/00* (2013.01); *C11B 9/0015* (2013.01); *C11B 9/0019* (2013.01); *C11B 9/0034* (2013.01); *C11B 9/0038* (2013.01); *C11B 9/0053* (2013.01); *C11B 9/0061* (2013.01); *C11B 9/0076* (2013.01); *C11B 9/008* (2013.01); *C11B 9/0084* (2013.01); *C11D 3/2093* (2013.01); *C11D 3/50* (2013.01); *A61K 8/33* (2013.01); *A61K 8/34* (2013.01); *A61K 8/35* (2013.01); *A61Q 5/02* (2013.01); *A61Q 19/10* (2013.01)

(58) Field of Classification Search
CPC ....................................................... C11B 9/003
USPC ............................................................. 512/8
See application file for complete search history.

(56) References Cited

U.S. PATENT DOCUMENTS 3,978,108 A * 8/1976 Teisseire et al. ............ 560/122
4,584,127 A * 4/1986 Uijttewaal et al. ............. 512/8

OTHER PUBLICATIONS

Horclois ("Cyclopentadiene: commercial extraction of coal byproducts: new uses", Chimie et Industries, Paris, 1934, Special No. 357-63).*
English Translation of the Abstract of Horclois ("Cyclopentadiene: commercial extraction of coal byproducts: new uses", Chimie et Industries, Paris, 1934, Special No. 357-63). Obtained Jul. 22, 2014 from EIC Search Results.*

* cited by examiner

*Primary Examiner* — Ling Choi
*Assistant Examiner* — Lanee Reuther
(74) *Attorney, Agent, or Firm* — Dilworth & Barrese, LLP

(57) ABSTRACT

A fragrance mixture, preferably perfume oil, is described, comprising the constituents (a) (cyclopent-2-enyl ethyl acetate)

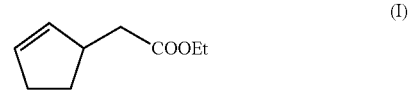

(I)

and additionally (b) one or a plurality of fragrances, preferably with a floral odor note, from the group consisting of alcohols and aldehydes with a molecular weight of 210 g/mol or less and/or (c) one or a plurality of fragrances from the group consisting of ketones, ethers and esters with a molecular weight in the range from 190 g/mol through 250 g/mol.

19 Claims, No Drawings

FRAGRANCE MIXTURES CONTAINING CYCLOPENT-2-ENYL ETHYL ACETATE

CROSS-REFERENCE TO RELATED APPLICATIONS

This application claims priority under 35 U.S.C. §119(e) to U.S. provisional application No. 61/570,632, filed Dec. 14, 2011 and European Application No. 11 193 578.9, filed on Dec. 14, 2011, the entire contents of which is hereby incorporated by reference.

The present invention relates to fragrance mixtures, preferably perfume oils, comprising a compound of formula (I) (cyclopent-2-enyl ethyl acetate)

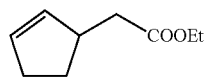
(I)

and additionally one or a plurality of further fragrances.

The present invention further relates to methods of producing fragrance mixtures according to the invention, in particular perfume oils, perfumed products containing a fragrance mixture according to the invention, methods of producing perfumed products according to the invention and the use of the compound of formula (I) for intensifying the natural freshness and/or aura and/or for masking or reducing oily, industrial and/or metallic notes of one or a plurality of fragrances different from the compound of formula (I).

The compound of formula (I) is known by a person skilled in the art, and a description of the odor of the compound of formula (I) is given in the book "S. Arctander, Perfume and Flavor Materials, Vol. I and II, Montclair, N. J., 1969, self-published" under number 1205.

The compound of formula (I) is described there as strong, fresh-fruity with a note of an overripe pineapple. It can also be seen from this textbook that the compound of formula (I) is used in some flavoring mixtures. Up to now, the compound of formula (I) has not found any notable use in perfumery. The naming of particular quantitative proportions or particular odor effects in combination with fragrances of the constituents (b) or (c) has not previously been known.

The compound of formula (I) (cyclopent-2-enyl ethyl acetate; CAS No.: 15848-49-4) can be obtained for example by saponification and subsequent decarboxylation of 2-cyclopentene-1-malonic acid diethyl ester, which in its turn can be produced according to the synthesis specification of Moffet et al. (Organic Syntheses, Coll. Vol. 4, p. 291 (1963); Vol. 32, p. 52 (1952)).

Flower fragrances play an important role in perfumery. There is a constant need to stress (emphasize) particular odor aspects of a fragrance or of a fragrance mixture, and in the case of flower fragrances this applies in particular to their natural freshness and aura. There is also a constant need to mask or reduce particular odor aspects of a fragrance or of a fragrance mixture, and in the case of flower fragrances this applies in particular to oily and industrial notes.

The object to be achieved by the present invention was to stress or emphasize particular odor aspects of particular fragrances or fragrance mixtures and/or to mask or reduce particular odor aspects of a fragrance or of a fragrance mixture, in particular oily and industrial notes.

This object is achieved by a fragrance mixture, preferably by a perfume oil, comprising the constituents
(a) compound of formula (I)

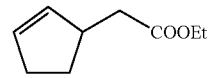
(I)

and additionally:
(b) one or a plurality of fragrances, preferably with a floral odor note, from the group consisting of alcohols and aldehydes with a molecular weight of 210 g/mol or less and/or
(c) one or a plurality of fragrances from the group consisting of ketones, ethers and esters with a molecular weight in the range from 190 g/mol through 250 g/mol.

Fragrance mixtures according to the invention are regularly liquid at 25° C. and 1013 hPa and are usually homogeneous solutions.

Surprisingly, in a fragrance mixture according to the invention, the compound of formula (I) has the effect that particular odor aspects of the fragrance or fragrances of component (b) and/or of the fragrance or fragrances of component (c) are stressed or emphasized and/or are masked or reduced. In particular, oily and industrial notes of the fragrances of components (b) and/or (c) are effectively masked or reduced by the compound of formula (I).

In a fragrance mixture according to the invention (for example a perfume oil), a person skilled in the art will select the proportion of component (a), i.e. the proportion of the compound of formula (I), so that the effect he desires of stressing (emphasizing) and/or masking or reducing an odor note is achieved, and he will take care not to use an excessive amount of component (a), which could dominate the overall sensory impression of a fragrance mixture and conversely not provide such a small amount of component (a) that a stressing or masking/reduction of odor aspects of fragrances of component (b) or (c) is not or is barely still perceptible. Regarding preferred proportions of concentrations, see the following explanations and the appended examples.

Surprisingly it was found that, over and above its primary sensory properties, the compound of formula (I) has additional positive secondary properties, e.g. high stability in certain conditions of application (in alkaline media (washing powder, fabric softener, soap, shampoo etc.), a high yield, a good adherence, and a high substantivity. This property is for an ester with a molar weight of 154 g/mol.

Constituent (b) of a Fragrance Mixture According to the Invention

Constituent (b) of the fragrance mixture according to the invention comprises one or a plurality of fragrances from the group consisting of alcohols and aldehydes with a molecular weight of 210 g/mol less. Preferably these fragrances have a floral odor note. Such fragrances are known by a person skilled in the art; Alcohols and aldehydes (also those with a floral odor note) represent a very important fragrance group in perfumery.

Fragrance mixtures according to the invention, preferably perfume oils, are preferred, wherein the constituent (b) contains two, three, four, five or more different fragrances.

Preferably, in a fragrance mixture according to the invention the weight ratio of the total amount of fragrances of constituent (b) to the compound of formula (I) is greater than or equal to 99:1, preferably greater than or equal to 99.9:0.1, particularly preferably greater than or particularly preferably equal to 99.999:0.001.

In our own investigations it was found that these weight ratios are particularly advantageous. At these weight ratios, the intrinsic odor of the compound of formula (I) is regularly no longer or barely still perceptible, nevertheless the presence of the compound of formula (I) has a positive influence on the overall note of the fragrance mixture according to the invention. It is particularly surprising that even at low concentrations the compound of formula (I) has an effect on the freshness and aura of the fragrance mixture, without bringing about or emphasizing a fruity odor to a relevant extent.

Fragrance mixtures according to the invention, preferably perfume oils according to the invention, are particularly preferred, wherein the fragrance or fragrances of constituent (b) are selected from the group consisting of 2-methyl-3-(4-tert-butylphenyl)propanal, 4-(4-hydroxy-4-methylpentyl)-3-cyclohexenecarboxaldehyde, 2-methyl-4-(2,2,6-trimethyl-1-cyclohexen-1-yl)-2-butenal, 1-methyl-4-(4-methyl-3-penten-1-yl)-3-cyclohexene-carboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-dimethyl-3-m-tolyl-propan-1-ol, 1-(4-isopropyl-cyclohexyl)-ethanol, (4-isopropyl-cyclohexyl)-methanol, 2-phenylethanol, 2-isobutyl-4-methyl-tetrahydropyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylene oct-7-en-2-ol and (E/Z)-3,7-dimethyl-nona-1,6-dien-3-ol.

Fragrances according to the invention, preferably perfume oils according to the invention, are particularly preferred wherein the fragrance or fragrances of constituent (b) are selected from the group consisting of 1-(4-isopropyl-cyclohexyl)-ethanol(mugetanol), (E)-3,7-dimethyl-octa-2,6-dien-1-ol(geraniol), 3,7-dimethyl-oct-6-en-1-ol(citronellol), (4-isopropyl-cyclohexyl)-methanol(mayol), 2-methyl-6-methylene oct-7-en-2-ol(myrcenol) (2-methyl-6-methylene oct-7-en-2-ol) and 2,6-dimethyl-oct-7-en-2-ol(dihydromyrcenol).

Fragrance mixtures according to the invention, preferably perfume oils according to the invention, are preferred wherein the, a plurality of or all fragrances of constituent (b) each have a molecular weight in the range from 140 through 170 g per mol.

Fragrance mixtures according to the invention, preferably perfume oils according to the invention, are quite particularly preferred in which the constituent (b) is an alcohol.

Surprisingly, the sensory properties of fragrances of component (b) are influenced positively by combining with an amount of the compound of formula (I). In an individual case, the sensory impression is shifted towards more natural, more fresh, more floral, more aura, less industrial, less oily and/or less metallic, of course also with other sensory effects being observed in an individual case. Detailed odor descriptions are given in the appended examples.

Constituent (c) of a Fragrance Mixture According to the Invention

Fragrance mixtures according to the invention, preferably perfume oils, are preferred wherein the constituent (c) contains two, three, four, five or more different fragrances.

The fragrances of the constituent (c) function regularly as base notes of a fragrance mixture according to the invention or of a perfume oil according to the invention.

Preferably the fragrances of the constituent (c) are ketones, ethers and/or esters with a molecular weight in the range from 196 g/mol through 250 g/mol.

Compounds with a molecular weight between 190 and 210 g/mol, which belong both to the group of aldehydes and/or alcohols and to the group of ketones, esters and/or ethers, are assigned both to the constituent (b) and to the constituent (c).

Fragrance mixtures according to the invention, preferably perfume oils according to the invention, are particularly preferred in which the weight ratio of the total amount of fragrances of the constituent (c) to the compound of formula (I) is greater than or equal to 99:1, preferably greater than or equal to 99.9:0.1, particularly preferably is greater than or equal to 99.999:0.001.

In our own investigations it was found that these weight ratios are particularly advantageous. At these weight ratios, the intrinsic odor of the compound of formula (I) regularly is no longer or barely still perceptible, however the presence of the compound of formula (I) exerts a positive influence on the overall note of the fragrance mixture according to the invention. It is particularly surprising that even at low concentrations, the compound of formula (I) has an effect on the freshness and aura of the fragrance mixture, without bringing about or emphasizing a fruity odor to a relevant extent.

Examples of fragrances with a molar weight in the range from 190 g/mol through 250 g/mol, which can form part of the constituent (c), are known by a person skilled in the art and for example can be found in S. Arctander, Perfume and Flavor Materials, Vol. I and II, Montclair, N.J., 1969, self-published or H. Surburg, J. Panten, "Common Fragrance and Flavor Materials", 5th edition, Wiley-VCH, Weinheim 2006.

Fragrance mixtures according to the invention, preferably perfume oils according to the invention, are particularly preferred wherein the fragrance or fragrances of the constituent (c) are selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyllinalyl acetate, cedrylmethyl ether, cedrylmethyl ketone, cedryl acetate, (4aR,5R,7aS,9R)-octahydro-2,2,5,8,8,9a-hexamethyl-4H-4a,9-methano azuleno(5,6-d)-1,3-dioxol), 1',1',5',5'-tetramethyl-hexahydro-spiro[1,3-dioxolan-2,8'(5'H)-2H-2,4a]methano-naphthalene, cyclododecylmethyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexylpropionate, allylcyclohexyloxyacetate, benzylbenzoate, benzylcinnamate, oxacyclohexadecan-2-one, 15-hydroxy-pentadecanoic acid lactone, 5-cyclohexadecen-1-one, 3-methyl-cyclopentadecenone, 1,3,4,6,7,8-hexahydro-4,6,6,7,8,8-hexamethyl cyclopenta[g]-2-benzopyran, 2-[1-(3,3-dimethylcyclohexyl)ethoxy]-2-methyl-,1-propanoate, 1,4-dioxacycloheptadecane-5,17-dione, 3-methyl-cyclopentadecanone, 8-cyclohexadecen-1-one, 3a,6,6,9a-tetramethyl dodecahydronaphtho[2,1-b]furan, alpha-irone, beta-irone, alpha-n-methylionone, beta-n-methylionone, alpha-isomethylionone, beta-isomethylionone and allylionone.

Particularly preferred fragrance mixtures according to the invention are those in which constituent (c) contains methyl dihydrojasmonate or consists of methyl dihydrojasmonate.

Particularly preferred fragrance mixtures according to the invention, preferably perfume oils according to the invention, in which constituent (c) contains methyl dihydrojasmonate or consists of methyl dihydrojasmonate, are those in which the content of cis-methyl dihydrojasmonate is more than 30 wt %, more preferably more than 60 wt %, particularly preferably more than 75 wt % and quite particularly preferably more than 90 wt %, in each case relative to the total weight of cis- and trans-methyl dihydrojasmonate.

In our own investigations it was found that fragrance mixtures according to the invention, in particular perfume oils, in which constituent (c) contains methyl dihydrojasmonate or consists of methyl dihydrojasmonate, impart a particularly preferred odor impression owing to the presence of the compound of formula (I). The compound of formula (I) brings about a harmonization and rounding-off of the individual odor of methyl dihydrojasmonate and interacts to bring about a natural floral odor of white blossoms. The jasmine notes of the methyl dihydrojasmonate are stressed in a unique manner, so that the whole composition seems more valuable.

Surprisingly, the sensory properties of fragrances of component (c) are influenced positively by combining with an amount of the compound of formula (I). In an individual case the sensory impression is shifted towards more natural, more fresh, more floral, more aura, less industrial, less oily and/or less metallic, and of course other sensory effects were also observed in an individual case. Detailed odor descriptions are given in the appended examples.

In fragrance mixtures according to the invention, the compound of formula (I) is of course used at least in such an amount that a sensory effect is achieved. A sensory effect is achieved through the presence of the compound of formula (I) when a comparative fragrance mixture, which with otherwise identical composition does not contain a compound of formula (I), in sensory testing is assessed differently from the fragrance mixture according to the invention.

Preferably the compound of formula (I) is used in a fragrance mixture according to the invention in a concentration such that the sensory impression of the fragrance mixture according to the invention is more natural, fresher, more floral, possesses more aura, is less industrial, less oily and/or less metallic than the sensory impression of a comparative fragrance mixture, which with otherwise identical composition does not contain a compound of formula (I).

Preferably the weight ratio of the total amount of fragrances of the constituents (b) and (c) to the compound of formula (I) is less than or equal to 99.999:0.0001.

Fragrance mixtures according to the invention, in particular perfume oils according to the invention, can be used in liquid form, undiluted or diluted with a solvent, for perfuming or aromatizing. Suitable solvents for this are in particular ethanol, glycerol, 1,2-propylene glycol, 1,2-butylene glycol, dipropylene glycol, diethyl phthalate, triethyl citrate, isopropyl myristate and triacetin.

Alcohols and aldehydes with a molecular weight of 210 g/mol or less and ketones, ethers and esters with a molecular weight in the range from 190 g/mol through 250 g/mol are not counted among the constituents (b) or (c), if it is a compound selected from the group consisting of ethanol, isopropanol, glycerol, 1,2-propylene glycol, 1,2-butylene glycol, dipropylene glycol, diethyl phthalate and triacetin.

Fragrance mixtures according to the invention, preferably perfume oils according to the invention, are preferably combined with further constituents. Preferred further constituents are selected from the group consisting of:

preservatives, preferably those mentioned in US 2006/0089413, abrasives, anti-acne agents and agents for sebum reduction, preferably those mentioned in WO 2008/046791, agents against skin ageing, preferably those mentioned in WO 2005/123101, antibacterial agents, anticellulitis agents, anti-dandruff agents, preferably those mentioned in WO 2008/046795, anti-inflammatory agents, agents for preventing irritation, anti-irritants (anti-inflammatory, irritation-inhibiting and irritation-preventing agents), preferably those mentioned in WO 2007/042472 and US 2006/0089413, antimicrobial agents, preferably those mentioned in WO 2005/123101, antioxidants, preferably those mentioned in WO 2005/123101, astringents, antiseptic agents, antistatic agents, binders, buffers, carrier materials, preferably those mentioned in WO 2005/123101, chelating agents, preferably those mentioned in WO 2005/123101, cell stimulants, cleansing agents, care agents, depilatories, surfactants, deodorants and antiperspirants, preferably those mentioned in WO 2005/123101, plasticizers, emulsifiers, preferably those mentioned in WO 2005/123101, enzymes, essential oils, preferably those mentioned in US 2008/0070825, insect repellents, preferably those mentioned in WO 2005/123101, fibers, film formers, fixatives, foam formers, foam stabilizers, anti-foaming agents, foam boosters, fungicides, gelling agents and gel-forming agents, preferably those mentioned in WO 2005/123101, hair care agents, hair styling agents, hair straightening agents, moisture regulators (hydrating agents, moisturizers and/or humectants), preferably those mentioned in WO 2005/123101, osmolytes, preferably those mentioned in WO 2005/123101, compatible solutes, preferably those mentioned in WO 01/76572 and WO 02/15686, bleaching agents, strengthening agents, stain-removing agents, optical brighteners, impregnating agents, dirt repellents, friction-reducing agents, lubricants, moisture creams, ointments, opacifiers, plasticizers, concealers, polish, gloss, polymers, preferably those mentioned in WO 2008/046676, powders, proteins and protein hydrolysates, preferably those mentioned in WO 2005/123101 and WO 2008/046676, refatting agents, abrading agents, skin calming agents, skin cleaning agents, skin care agents, skin repair agents, preferably containing cholesterol and/or fatty acids and/or ceramides and/or pseudoceramides, here preferably those mentioned in WO 2006/053912, skin lightening agents, preferably those mentioned in WO 2007/110415, skin protectants, skin softening agents, skin cooling agents, preferably those mentioned in WO 2005/123101, skin warming agents, preferably those mentioned in WO 2005/123101, stabilizers, UV-absorbing agents and UV filters, preferably those mentioned in WO 2005/123101, benzylidene-beta-dicarbonyl compounds, preferably those mentioned in WO 2005/107692, alpha-benzoylcinnamic acid nitriles, preferably those mentioned in WO 2006/015954, AhR-receptor antagonists, preferably those mentioned in WO 2007/128723 and WO 2007/060256, detergents, fabric softeners, suspending agents, skin tanning agents, preferably those mentioned in WO 2006/045760, thickening agents, vitamins, preferably those mentioned in WO 2005/123101, oils, waxes and fats, preferably those mentioned in WO 2005/123101, phospholipids, preferably those mentioned in WO 2005/123101, fatty acids (saturated fatty acids, mono- or polyunsaturated fatty acids, α-hydroxy acids, polyhydroxy fatty acids), preferably those mentioned in WO 2005/123101, liquefiers, dyes and color-protecting agents and pigments, preferably those mentioned in WO 2005/123101, anticorrosive agents, aromas and flavoring materials and further additional fragrances, preferably those listed in S. Arctander, Perfume and Flavor Chemicals, self-published, Montclair, N.J., 1969 and Surburg, Panten, Common Fragrance and Flavor Materials, 5th edition, Wiley-VCH, Weinheim 2006, in particular the further fragrances explicitly mentioned in US 2008/0070825, which are not already part of constituents (b) and (c) of a fragrance mixture according to the invention or of a perfume oil according to the invention, alcohols and polyols, preferably those mentioned in WO 2005/123101, surfactants, preferably those mentioned in WO 2005/123101, animal extracts, yeast extracts, extracts of algae or microalgae, electrolytes, liquefiers, organic solvents, preferably those mentioned in WO 2005/123101, or silicones and silicone derivatives, preferably those mentioned in WO 2008/046676. Compounds that come under the definition of constituents (b) and/or (c), however, are assigned to these constituents regardless of the application; regarding exceptions for certain solvents, see above.

Moreover, fragrance mixtures according to the invention, in particular perfume oils according to the invention, can be adsorbed on a carrier, which provides both fine distribution of the fragrances contained therein in the product and controlled release during use. Said carriers can be porous inorganic materials such as light sulfate, silica gels, zeolites, gypsums, clays, clay granules, gas concrete etc. or organic materials such as wood, cellulose-based substances, sugars, dextrins (e.g. maltodextrin) or plastics such as PVC, polyvinyl acetates or polyurethanes. The combination of fragrance mixture according to the invention and carrier is an example of a product according to the invention.

Fragrance mixtures according to the invention, in particular perfume oils according to the invention, can also be microencapsulated, spray-dried, can be in the form of inclusion complexes or extrusion products (i.e. products according to the invention) and can be added in this form e.g. to a product to be perfumed.

Optionally, the properties of the compositions modified in this way can be further optimized by so-called "coating" with suitable materials with a view to more selective release of the fragrance, for which preferably wax-like plastics, e.g. polyvinyl alcohol, are used. The resultant products are in their turn products according to the invention.

The microencapsulation of the fragrance mixtures according to the invention, preferably of the perfume oils according to the invention, can be carried out for example by the so-called coacervation process by means of encapsulating materials e.g. of polyurethane-like substances or soft gelatin. The spray-dried compositions of fragrances or flavoring materials can be produced for example by spray-drying an emulsion or dispersion containing the fragrance mixture according to the invention, preferably a perfume oil, wherein modified starch, proteins, dextrin and plant gums can be used as carriers. Inclusion complexes can be produced for example by introducing dispersions of the fragrance mixture according to the invention, preferably of a perfume oil according to the invention, and cyclodextrins or urea derivatives into a suitable solvent, e.g. water. Extrusion products can be obtained by melting a fragrance mixture according to the invention, preferably a perfume oil according to the invention, with a suitable wax-like substance and by extrusion followed by solidification, optionally in a suitable solvent, e.g. isopropanol.

The invention further relates to a method of producing a fragrance mixture according to the invention, preferably a perfume oil according to the invention, characterized by the following step:
    mixing the constituent (a) with constituent (b) and/or constituent (c).

A method according to the invention is preferred in which the result is a fragrance mixture according to the invention, preferably a perfume oil according to the invention, in which
    the weight ratio of the total amount of fragrances of constituent (b) to the compound of formula (I) is greater than or equal to 99:1, preferably greater than or equal to 99.9:0.1, particularly preferably is greater than or equal to 99.999:0.001,
    and/or
    the weight ratio of the total amount of fragrances of the constituent (c) to the compound of formula (I) is greater than or equal to 99:1, preferably greater than or equal to 99.9:0.1, particularly preferably is greater than or equal to 99.999:0.001.

It was found that the corresponding proportions by weight are particularly advantageous. Reference should be made to the above explanations.

The invention further relates to a method for intensifying the natural freshness and/or aura and/or for masking or reducing oily, industrial and/or metallic notes of one or a plurality of fragrances different from the compound of formula (I), in particular one or a plurality of fragrances different from the compound of formula (I) with a floral odor note, in particular jasmine, comprising the following step:
    mixing the fragrance or fragrances different from the compound of formula (I) with an amount of compound of formula (I) that is sufficient to intensify the natural freshness and/or aura of the fragrance or fragrances different from the compound of formula (I) and/or to mask or reduce oily, industrial and/or metallic notes.

Said method according to the invention is preferred in which the fragrance or fragrances different from the compound of formula (I) are selected from the constituents (b) and/or (c) of a fragrance mixture according to the invention.

In said preferred methods, preferably
    the weight ratio of the total amount of fragrances of the constituent (b) to the compound of formula (I) is greater than or equal to 99:1, preferably greater than or equal to 99.9:0.1, particularly preferably is greater than or equal to 99.999:0.001
    and/or
    the weight ratio of the total amount of fragrances of the constituent (c) to the compound of formula (I) is greater than or equal to 99:1, preferably greater than or equal to 99.9:0.1, particularly preferably is greater than or equal to 99.999:0.001.

The above statements regarding preferred fragrance mixtures according to the invention apply correspondingly to the methods according to the invention.

The invention also relates to a perfumed product containing a fragrance mixture according to the invention, preferably a perfume oil according to the invention, wherein the fragrance mixture is preferably contained in a sensorially effective amount in the perfumed product.

"Sensorially effective amount" means, in the present context, that the perfumed product according to the invention allows the sensory properties of the fragrance mixture according to the invention to be discerned during operation or use.

Preferred perfumed products according to the invention are selected from the group consisting of: perfume extracts, eaux de parfum, eaux de toilette, shaving lotions, eaux de Cologne, pre-shave products, splash Colognes, perfumed tissue wipes, acidic, alkaline and neutral cleansing agents, textile fresheners, ironing aids, liquid detergents, powdered detergents, laundry pretreatment agents, fabric softeners, washing soaps, washing tablets, disinfectants, surface disinfectants, air fresheners, aerosol sprays, waxes and polishes, body-care products, hand creams and lotions, foot creams and lotions, depilatory creams and lotions, after-shave creams and lotions, tanning creams and lotions, hair care products, deodorants and antiperspirants, decorative cosmetic products, candles, lamp oils, joss sticks, insecticides, repellents and propellants.

Particularly preferred perfumed products according to the invention are selected from the following list:
    eaux de parfum, eaux de toilette, shaving lotions (after-shave), eaux de Cologne, pre-shave products, splash Colognes;

acidic, alkaline and neutral cleansing agents, in particular for household use, preferably floor cleaners, window cleaners, dishwashing agents, bath and sanitary cleaners, liquid scouring agents, solid and liquid lavatory cleaners, powder and foam carpet cleaners, liquid detergents, powdered detergents, fabric softeners, surface disinfectants, in particular for hard surfaces (hard surface cleaners);

body-care products, preferably solid and liquid soaps, shower gels, shampoos, shaving soaps, shaving foams;

cosmetic emulsions of the oil-in-water, water-in-oil and water-in-oil-in-water type, preferably skin creams and lotions, face creams and lotions, sunscreen creams and lotions, after-sun creams and lotions, hand creams and lotions, foot creams and lotions, depilatory creams and lotions, after-shave creams and lotions, skin tanning creams and lotions, skin lightening creams and lotions;

hair care products, preferably hair sprays, hair gels, hair fixing lotions, hair rinses, permanent and semi-permanent hair dyes, hair lotions, hair creams and lotions;

deodorants and antiperspirants, preferably underarm sprays, roll-ons (preferably as alcoholic or non-alcoholic solution, as gel or (micro)emulsion), deodorant sticks (stick deodorants), deodorant creams.

Particularly preferred perfumed products according to the invention are washing and cleaning agents, hygiene or care products, in particular in the area of body and hair care, cosmetics and household products.

Preferred perfumed products according to the invention are those in which the proportion of the fragrance mixture according to the invention in the perfumed product is 0.01 through 10 wt %, preferably 0.1 through 5 wt % and particularly preferably 0.25 through 3 wt %, in each case relative to the total weight of the perfumed product. This applies in particular to the aforementioned preferred products.

The invention further relates to a method of producing a perfumed product comprising the steps:

i) providing a fragrance mixture according to the invention or producing a fragrance mixture by a method according to the invention, ii) providing the further constituents of the perfumed product and iii) bringing the further constituents of the perfumed product provided in step ii) in contact with a sensorially effective amount of the fragrance mixture provided in step i); wherein the amount of the compound of formula (I) is sufficient to intensify the natural freshness and/or aura of one, a plurality of or all of the fragrances of the constituents (b) and/or (c) and/or to mask or reduce oily, industrial and/or metallic notes or I) providing the constituents of the perfumed product, which are not constituents (a), (b) or (c) of a fragrance mixture according to the invention II) mixing the constituents of the perfumed product provided in step I) with the constituents (b) and/or (c) of a fragrance mixture according to the invention, to give a mixture in which the constituent or constituents (b) and/or (c) are present in a sensorially effective amount, III) bringing the mixture produced in step II) in contact with an amount of the compound of formula (I), wherein the amount of the compound of formula (I) is sufficient to intensify the natural freshness and/or aura of one, a plurality of or all of the fragrances of the constituents (b) and/or (c) and/or to mask or reduce oily, industrial and/or metallic notes.

Finally the invention also relates to the use of the compound of formula (I)

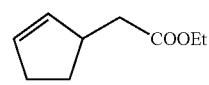

(I)

for intensifying the natural freshness and/or aura and/or for masking or reducing oily, industrial and/or metallic notes of one or a plurality of fragrances different from the compound of formula (I), in particular with a floral odor note, in particular jasmine.

A use according to the invention of the compound of formula (I) is preferred, wherein the fragrance or fragrances that are different from the compound of formula (I) are selected from the constituents (b) and/or (c) of a fragrance mixture according to the invention.

The following examples explain the invention; unless stated otherwise, proportions and percentages refer to weight.

Abbreviations Used:

Dipropylene glycol (DPG), diethyl phthalate (DEP), triethyl citrate (TEC), isopropyl myristate (IPM); nat.=natural;

HEDIONE® HC/30 contains at least 30 wt % of the cis-isomer and about 70 wt % of the trans-isomer of methyl dihydrojasmonate.

For explanations of the product names of the fragrances, see e.g. S. Arctander, Perfume and Flavor Materials, Vol. I and II, Montclair, N.J., 1969, self-published or H. Surburg, J. Panten, "Common Fragrance and Flavor Materials", 5th edition, Wiley-VCH, Weinheim 2006.

EXAMPLES

1. Example

Perfume Oil P1

| Preferred use: All-purpose cleaner 0.4% | |
|---|---|
| Aldehyde C 8 | 20.00 |
| Aldehyde C11 MOA | 10.00 |
| Limonenal | 2.00 |
| Mintonat | 120.00 |
| Dihydro Myrcenol | 50.00 |
| Lemon Oil | 10.00 |
| Litsea Cubeba Oil | 40.00 |
| Citronitrile | 10.00 |
| Eucalyptus Oil Citriodora | 50.00 |
| Citronella Oil | 40.00 |
| Orange Oil | 130.00 |
| Terpineol | 20.00 |
| Lavandin Oil | 50.00 |
| Rosemary Oil | 5.00 |
| Eucalyptus Oil | 5.00 |
| Aromabase Apple Green | 20.00 |
| Rosaphen ® | 20.00 |
| Benzyl Acetate | 150.00 |
| Coumarin | 20.00 |
| Timberide | 2.00 |
| Dipropylene Glycol | 226.00 |
| | 1000.00 |

With addition of 0.5% of a 0.1% solution of cyclopent-2-enyl ethyl acetate, the mixture is more rounded, more harmonious, more natural, stronger and no longer so industrial.

With addition of 1% of a 0.1% solution of cyclopent-2-enyl ethyl acetate, the mixture becomes stronger in the top note and produces an additional mandarin note.

2. Example

Perfume Oil P2

| Preferred use: Shower gel 0.5% | |
|---|---|
| Limonenal 10% | 4.00 |
| Florazon | 1.00 |
| Leafovert ® | 6.00 |
| Vertocitral | 14.00 |
| Phenylacetald. Dimethyl Acetal | 10.00 |
| Cyclogalbant ® | 10.00 |
| Floropal | 7.00 |
| Mintonat | 50.00 |
| Lemongrass Oil Rect. | 8.00 |
| Orange Oil | 40.00 |
| Claritone ® | 15.00 |
| Rosemary Oil | 5.00 |
| Artemisia Oil | 5.00 |
| Thyme Oil White | 1.00 |
| Pine Needle Oil | 4.00 |
| Hexyl Acetate | 20.00 |
| Ethyl Methyl Butyrate-2 | 2.00 |
| Allyl Cyclohexyl Propionate | 3.00 |
| Peach Total | 1.00 |
| Melon Concentrate | 12.00 |
| Lilax Soft | 100.00 |
| Linalool | 55.00 |
| Geranium RCO | 7.00 |
| Phenylethyl Alcohol | 60.00 |
| Geraniol Supra | 70.00 |
| Geranyl Acetate Pure | 20.00 |
| Benzyl Acetate | 24.00 |
| Hedione | 90.00 |
| Hexyl Cinnamic Aldehyde Alpha | 60.00 |
| Hexenyl Salicylate Cis-3 | 60.00 |
| Parmanyl ® | 3.00 |
| Isoeugenol | 2.00 |
| Coumarin | 3.00 |
| Vetikolacetat ® | 2.00 |
| Corps Racine 0.1% | 7.00 |
| Evernyl 10% | 14.00 |
| Ambrettolide | 5.00 |
| Globanone ® | 90.00 |
| Dipropylene Glycol | 110.00 |
| Triethyl Citrate | |
| | 1000.00 |

With addition of 0.5% of a 0.1% solution of cyclopent-2-enyl ethyl acetate, the mixture is more rounded, fresher.

With addition of 1% of a 0.1% solution of cyclopent-2-enyl ethyl acetate, the mixture has a more floral and stronger effect in the direction of white blossom.

3. Example

Perfume Oil P3

| Preferred use: Fabric softener 0.8% | |
|---|---|
| Aldehyde C11 Undecylenic 10% | 15.00 |
| Florazon | 10.00 |
| Mintonat | 10.00 |
| Dihydro Myrcenol | 40.00 |
| Mandaril 10% | 10.00 |
| Orange Oil | 70.00 |
| Nerolione 10% | 15.00 |
| Majantol ® | 60.00 |
| Tetrahydro Linalool | 50.00 |
| Phenylethyl Alcohol | 70.00 |
| Citronellol 950 | 50.00 |
| Citronellyl Acetate Extra | 20.00 |
| Isodamascon ® 10% | 10.00 |
| Benzyl Acetate | 30.00 |
| Hedione | 30.00 |
| Hexyl Cinnamic Aldehyde Alpha | 20.00 |
| Hexyl Salicylate | 100.00 |
| Eugenol | 10.00 |
| Heliotropin | 20.00 |
| Ethyl Vanillin 10% | 30.00 |
| Herbyl Propionate | 100.00 |
| Iso E Super | 100.00 |
| Patchouli Oil | 10.00 |
| Timberide | 5.00 |
| Corps Racine 0.1% | 7.00 |
| Evernyl 10% | 5.00 |
| Galaxolide Type Base | 100.00 |
| Triethyl Citrate | 3.00 |
| | 1000.00 |

With addition of 0.5% of a 0.1% solution of cyclopent-2-enyl ethyl acetate, the mixture is more rounded, no longer so industrial and more natural.

With addition of 1% of a 0.1% solution of cyclopent-2-enyl ethyl acetate the mixture has a more floral and stronger effect in the direction of white blossom.

4. Example

Perfume Oil P4

| Preferred use: Fabric softener 0.8% | |
|---|---|
| Aldehyde C12 | 5.00 |
| Alcohol C 6 | 10.00 |
| Dihydro Myrcenol | 30.00 |
| Claritone ® | 10.00 |
| Petitgrain Oil Parag. | 5.00 |
| Methyl Naphthyl Ketone Beta Cryst | 10.00 |
| Lavandin Grosso | 20.00 |
| Rosemary Oil Tun. | 10.00 |
| Hexyl Acetate | 5.00 |
| Cyclamen Aldehyde | 10.00 |
| Mugetanol ® | 40.00 |
| Majantol ® | 30.00 |
| Tetrahydro Muguol | 20.00 |
| Base Muguet B | 20.00 |
| Tetrahydro Linalool | 40.00 |
| Dimethyl Benzyl Carbinyl Acetate | 30.00 |
| Terpineol Pure | 20.00 |
| Rose Oxide HC 10% | 20.00 |
| Phenyl Ethyl Alcohol | 60.00 |
| Base Rose Pamela-Y | 30.00 |
| Tetrahydrogeraniol | 10.00 |
| Isodamascon ® 10% | 20.00 |
| Benzyl Acetone | 40.00 |
| Hexyl Salicylate | 140.00 |
| Parmanyl ® 10% | 10.00 |
| Ionone Beta | 10.00 |
| Isoraldeine | 50.00 |
| Base Ylang B | 15.00 |
| Anisic Aldehyde Pure | 10.00 |
| Herbaflorat | 30.00 |
| Herbyl Propionate | 60.00 |
| Iso E Super | 120.00 |
| Sandel 80 | 20.00 |
| Ysamber ® K | 10.00 |

| Preferred use: Fabric softener 0.8% | |
|---|---:|
| Globanone ® | 30.00 |
| Dipropylene glycol | |
| | 1000.00 |

With addition of 0.5% of a 0.1% solution of cyclopent-2-enyl ethyl acetate, the mixture is more rounded, more floral and tends in the direction of lavender.

With addition of 1% of a 0.1% solution of cyclopent-2-enyl ethyl acetate the mixture obtains more volume and has a stronger effect in the direction of white blossom.

5. Example

Perfume Oil P5

| Preferred use: Body Lotion 0.3% | |
|---|---:|
| Aldehyde C14 SOG | 5.00 |
| Allylamyl glycolate | 2.00 |
| Allylcyclohexyl propionate | 2.00 |
| Allyl heptylate | 5.00 |
| Allyl ionone | 1.00 |
| Ambroxide 10% IPM | 4.00 |
| Benzyl acetate | 2.00 |
| Benzyl salicylate | 21.50 |
| Bourgeonal | 4.00 |
| Damascon alpha 10% DPG | 1.00 |
| Dihydromyrcenol | 20.00 |
| Dimethylbenzylcarbinyl acetate | 10.00 |
| Farenal | 1.00 |
| Frambinon 10% DPG | 3.00 |
| Geranyl acetate pure | 4.00 |
| Hedione | 200.00 |
| Indoflor crist 10% DPG | 5.50 |
| Ionone alpha | 10.00 |
| Iso E Super | 40.00 |
| Jasmon cis | 1.00 |
| Leafovert | 2.00 |
| Macrolide supra | 30.00 |
| Majantol | 50.00 |
| Manzanate 10% IPM | 4.00 |
| Mayol | 55.00 |
| Methylphenyl acetate 10% DPG | 2.00 |
| Mintonat | 5.00 |
| Nonadienal trans,cis-2,6 5% TEC 1% DPG | 2.00 |
| Patchouli oil defatted | 2.00 |
| Phenylethyl alcohol | 15.00 |
| Phenylethyl dimethylcarbinol | 7.00 |
| Rosaphen | 20.00 |
| Rose Oxide L 1% DPG | 5.00 |
| Sandranol | 5.00 |
| Tetrahydromuguol | 40.00 |
| Undecavertol | 2.00 |
| Veloutone 10% DPG | 3.00 |
| Vertocitral | 2.00 |
| Vertomugual | 1.00 |
| Dipropylene glycol | 406.00 |
| | 1000.00 |

With addition of 0.5% of a 0.1% solution of cyclopent-2-enyl ethyl acetate, the mixture is more rounded, fresher and more natural.

With addition of 1% of a 0.1% solution of cyclopent-2-enyl ethyl acetate the mixture obtains more volume and has a stronger effect in the direction of white blossom (jasmine).

6. Example

Odor Description of Preferred Fragrances After Adding Cyclopent-2-enyl Ethyl Acetate

| Fragrances | Type | Weight ratio of the fragrance to the compound of formula (I) (0.1% in DPG) | Odor description compared with the odor of the pure fragrance |
|---|---|---|---|
| Mugetanol (M = 170) | Alcohol | 100:0.5 100:0.1 | softer, more natural, more floral |
| Dihydromyrcenol (M = 156) | Alcohol | 99:1.0 | less industrial, more natural-lavender-like, more floral |
| Linalool (M = 154) | Alcohol | 99:1.0 | less industrial, fresher, more natural |
| Geraniol (M = 154) | Alcohol | 99:1.0 | less oily, less metallic, more rounded, more natural, more volume |
| Citronellol (M = 156) | Alcohol | 100:0.5 100:1.0 | less oily, more natural, more rosy |
| Phenoxanol (M = 178) | Alcohol | 100:1.0 100:2.0 | less industrial, more rosy, more natural |
| Lilial ® (M = 204) | Aldehyde | 100:1.0 | less industrial, fresher, more natural, stronger lily of the valley effect |
| Aldehyde MNA (M = 184) | Aldehyde | 100:1.0 | less oily, less metallic, more rounded |
| Melonal ® (M = 140) | Aldehyde | 100:1.0 | less industrial, less metallic, more rounded, more natural |
| Hedione ® (M = 226) | Ketone/Ester | 100:1.0 | less oily, more floral, more rounded, more natural, stronger jasmine effect |
| para tert.-Butyl-cyclohexanone (M = 154) | Ketone | 100:1.0 | less industrial, more rounded, more harmonious |
| Oryclon ® (M = 198) | Ester | 100:1.0 | less industrial, more rounded, more harmonious, fresher |

7. Example

Odor Description of Preferred Fragrance Mixtures after Adding cyclopent-2-enyl ethyl acetate

| Fragrances | Type | Weight ratio of alcohol to Hedione | Odor description in a 0.1% DPG solution with addition of 1 g of compound of formula (I) per 100 g of the alcohol/Hedione mixture compared to the odor of the pure fragrance mixture |
|---|---|---|---|
| Mayol Hedione | Alcohol + ketone/ester | 1:1 | softer, more natural, more floral, more jasmine |
| Dihydro-myrcenol Hedione | Alcohol + ketone/ester | 3:1 | fresher, more floral, more lavender-like, more natural |

The perfume oils P1, P2, P3, P4 or P5 from the above perfume oil examples 1 to 5 were incorporated in each case separately in the following formulations.

The odor effects described above for the respective perfume oil were in each case also observed in the following formulations.

Formulation Examples

Example F1

Washing Powder

| Material | Chemical name | Function | wt % | wt % |
|---|---|---|---|---|
| Sodium metasilicate pentahydrate | Sodium metasilicate pentahydrate | | to 100 | to 100 |
| Sodium hydrogen carbonate | Sodium hydrogen carbonate | Alkali | 15.0 | 15.0 |
| Sodium percarbonate | Sodium carbonate peroxyhydrate | Bleach | 15.0 | 15.0 |
| Peractive AC Blue | TAED/Na-carboxymethyl-cellulose | Activator | 5.00 | 5.00 |
| Genapol OA-080 | Oxoalcohol C14-15, 8EO | Non-ionic surfactant | 3.00 | 3.00 |
| Texapon K12 powder | Sodium lauryl sulfate C12 | Anionic surfactant | 7.00 | 7.00 |
| Tinopal CBS-X | | Brightener | 0.50 | 0.50 |
| Savinase 6.0 T, type W | Protease | Enzyme | 0.40 | 0.40 |
| Termamyl 120 T | Alpha-amylase | Enzyme | 0.30 | 0.30 |
| Sodium sulfate | Sodium sulfate | Filler | 5.50 | 5.50 |
| Perfume Oil P1, P2, P3, P4 or P5 | | Perfume (fragrance) | 0.30 | 0.50 |

Example F2

All-Purpose Cleaner

| Material | Chemical name | Function | wt % | wt % |
|---|---|---|---|---|
| Deionized water | Water | Solvent | to 100 | to 100 |
| Mergal K9N | 5-Chloro-2-methyl-3-(2H)-isothiazolone and 2-methyl-3-(2H)-isothiazolone | Preservative | 0.1 | 0.1 |
| Trisodium citrate dihydrate | Trisodium citrate dihydrate | Complexing agent | 3.0 | 3.0 |
| Zetesol NL-2 | Fatty alcohol C12-14-sulfate, sodium | Anionic surfactant | 30.0 | 30.0 |
| Imbentin C/125/055 | Fatty alcohol C12-C15, 8EO | Non-ionic surfactant | 5.0 | 5.0 |
| Ethanol | Ethanol | Solvent | 2.0 | 2.0 |
| Perfume Oil P1, P2, P3, P4, or P5 | | Perfume (fragrance) | 0.3 | 0.5 |

Example F3

Shampoo

| Material | INCI name | wt % | wt % |
|---|---|---|---|
| Deionized water | Water | to 100 | to 100 |
| Plantacare PS 10 | Sodium Laureth Sulfate, Lauryl Glucoside | 20.0 | 20.0 |
| Euperlan PK 771 | Glycol Distearate, Sodium Lauryl Sulfate, Cocamide MEA, Laureth-10 | 6.0 | 6.0 |
| Dragocid Liquid | Phenoxyethanol, Methylparaben, Ethylparaben, Butylparaben, Propylparaben, Isobutylparaben | 0.5 | 0.5 |
| Sodium Chloride | Sodium Chloride | 1.4 | 1.4 |
| Citric Acid Monohydrate crystalline | Citric Acid | 0.1 | 0.1 |
| Perfume Oil P1, P2, P3, P4, or P5 | Perfume (Fragrance) | 0.5 | 0.8 |

Example F4

Shower Gel

| Material | INCI Name | wt % | wt % |
|---|---|---|---|
| Deionized Water | Water | to 100 | to 100 |
| Plantacare PS 10 | Sodium Laureth Sulfate, Lauryl Glucoside | 20.0 | 20.0 |
| Dragocid Liquid | Phenoxyethanol, Methylparaben, Ethylparaben, Butylparaben, Propylparaben, Isobutylparaben | 0.5 | 0.5 |
| Sodium Chloride | Sodium Chloride | 1.4 | 1.4 |
| Citric Acid Monohydrate crystalline | Citric Acid | 1.3 | 1.3 |
| Perfume Oil P1, P2, P3, P4, or P5 | Perfume (Fragrance) | 0.5 | 0.7 |

Example F5

Fabric Softener

| Material | Chemical Name | Function | wt % | wt % |
|---|---|---|---|---|
| Deionized Water | Water | Solvent | to 100 | to 100 |
| Rewoquat WE 18 | Dialkylester-ammonium ethosulfate | Cationic surfactant | 16.6 | 16.6 |
| Mergal K9N | 5-Chloro-2-methyl-3-(2H)-isothiazolone and 2-methyl-3-(2H)-isothiazolone | Preservative | 0.10 | 0.10 |
| Dow Corning 1520 Antifoam | Polydimethyl Siloxane | Anti-foaming agent | 0.30 | 0.30 |
| Magnesium Chloride 1% Solution | Magnesium Chloride Solution | Consistency agent | 10.00 | 10.00 |
| Perfume Oil P1, P2, P3, P4, or P5 | | Fragrance | 0.55 | 0.75 |

Example F6

Eau de Cologne/Eau de Toilette

| Ingredients | wt % | wt % |
|---|---|---|
| Perfume Oil P1, P2, P3, P4, or P5 | 5 | 10 |
| Ethanol | to 100 | to 100 |
| Water | 18 | 10 |

Example F7

Aerosol Pump Spray

| Ingredients | wt % | wt % |
|---|---|---|
| Perfume Oil P1, P2, P3, P4, or P5 | 1.0 | 1.5 |
| Ethanol | to 100 | to 100 |
| Water | 5.0 | 8.0 |
| Alpha-tocopherol | 0.20 | 0.20 |
| Hydroxypropylcellulose | 0.20 | — |
| Rosemary extract, ethanol-soluble | 0.22 | — |
| Cetyl alcohol | 1.00 | 0.50 |

Example F8

Shampoo

| Ingredients | wt % | wt % | wt % |
|---|---|---|---|
| Sodium lauryl ether sulfate (e.g. Texapon NSO, from Cognis Deutschland GmbH) | 12 | 12 | 12 |
| Cocamidopropyl betaine (e.g. Dehyton K, from Cognis Deutschland GmbH) | 2 | 2 | 2 |
| Sodium chloride | 1.4 | 1.4 | 1.4 |
| Citric acid | 1.3 | 1.3 | 1.3 |
| Phenoxyethanol, methyl-, ethyl-, butyl- and propylparaben | 0.5 | 0.5 | 0.5 |
| Perfume Oil P1, P2, P3, P4, or P5 | 0.3 | 0.5 | 0.7 |
| Water | to 100 | to 100 | to 100 |

Example F9

Washing Powder

| Ingredients | wt % | wt % | wt % |
|---|---|---|---|
| Linear Na-alkylbenzene sulphonate | 8.8 | 8.8 | 8.8 |
| Ethoxylated fatty alcohol C12-18 (7 EO) | 4.7 | 4.7 | 4.7 |
| Na-soap | 3.2 | 3.2 | 3.2 |
| Anti-foaming agent DOW CORNING(R) 2-4248S POWDERED ANTIFOAM, silicone oil on zeolite as carrier material | 3.9 | 3.9 | 3.9 |
| Zeolite 4A | to 100 | to 100 | to 100 |
| Na-carbonate | 11.6 | 11.6 | 11.6 |
| Na salt of a copolymer of acrylic and maleic acid (Sokalan CP5) | 2.4 | 2.4 | 2.4 |
| Na-silicate | 3.0 | 3.0 | 3.0 |
| Carboxymethylcellulose | 1.2 | 1.2 | 1.2 |
| Dequest 2066([[(phosphono-methyl)imino]bis[(ethylene-nitrilo)bis(methylene)]]tetrakis-phosphonic acid, sodium salt) | 2.8 | 2.8 | 2.8 |
| Optical brightener | 0.2 | 0.2 | 0.2 |
| Na-sulfate | 6.5 | 6.5 | 6.5 |
| Protease | 0.4 | 0.4 | 0.4 |
| Sodium perborate tetrahydrate | 21.7 | 21.7 | 21.7 |
| Perfume Oil P1, P2, P3, P4, or P5 | 0.25 | 0.35 | 0.5 |
| EDTA | 1.0 | 1.0 | 1.0 |

Example F10

Liquid Detergent

| Ingredients | wt % |
|---|---|
| Deionized water | 39.9 |
| Optical brightener | 0.10 |
| Coconut fatty acids (C12-C18) | 7.5 |
| Potassium hydroxide 50% solution | 4.3 |
| Propane-1,2-diol | 5.00 |
| Fatty alcohols C12-C15, 8 EO | 12.0 |
| Na-salt of secondary alkylsulphonates (C13-C17) | 17.0 |
| Triethanolamine | 2.0 |
| Trisodium citrate dihydrate | 5.0 |
| Dequest 2066([[(phosphonomethyl)imino]bis[(ethylene-nitrilo)bis(methylene)]]tetrakis-phosphonic acid, sodium salt) | 3.0 |
| Ethanol | 3.0 |
| Enzymes | 0.7 |
| Perfume Oil P1, P2, P3, P4, or P5 | 0.5 |

Example F11

Liquid Detergent Concentrate

| Ingredients | wt % |
|---|---|
| Deionized water | 13.4 |
| Coconut fatty acids (C12-C18) | 10.0 |
| Fatty alcohols C12-C15, 8 EO | 26.0 |
| Na-salt of secondary alkylsulphonates (C13-C17) | 26.5 |
| Triethanolamine | 8.5 |
| Na-salt of fatty alcohol sulfates C12-C14 | 3.0 |
| Ethanol | 5.5 |
| Urea | 4.5 |
| Enzymes | 0.9 |
| Citric acid | 1.0 |
| Perfume Oil P1, P2, P3, P4, or P5 | 0.7 |

The invention claimed is:

1. A fragrance mixture comprising:
(a) a compound of formula (I)

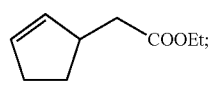

(I)

and
(b) at least one fragrance selected from the group consisting of alcohols and aldehydes, having a molecular weight of 210 g/mol or less; and/or
(c) at least one fragrance selected from the group consisting of ketones, ethers, and esters, having a molecular weight of 190 g/mol to 250 g/mol.

2. The fragrance mixture as claimed in claim 1, wherein constituent (b) consists of two or more different fragrances.

3. The fragrance mixture as claimed in claim 1, wherein the weight ratio of the total amount of fragrances of constituent (b) to the compound of formula (I) is greater than or equal to 99:1.

4. The fragrance mixture as claimed claim 1, wherein the one or more fragrances of constituent (b) are selected from the group consisting of 2-methyl-3-(4-tert-butylphenyl)propanal, 4-(4-hydroxy-4-methylpentyl)-3-cyclohexenecarboxaldehyde, 2-methyl-4-(2,2,6-trimethyl-1-cyclohexen-1-yl)-2-butenal, 1-methyl-4-(4-methyl-3-penten-1-yl)-3-cyclohexenecarboxaldehyde, 3-(3-isopropyl-phenyl)-butyraldehyde, (E)-2,6,10-trimethyl-undeca-5,9-dienal, benzo[1,3]-dioxole-5-carbaldehyde, 2,2-dimethyl-3-phenyl-propan-1-ol, 2,2-dimethyl-3-m-tolyl-propan-1-ol, 1-(4-isopropyl-cyclohexyl)-ethanol, (4-isopropyl-cyclohexyl)-methanol, 2-phenylethanol, 2-isobutyl-4-methyl-tetrahydropyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylene oct-7-en-2-ol and (E/Z)-3,7-dimethyl-nona-1,6-dien-3-ol.

5. The fragrance mixture as claimed in claim 1, wherein the one or more fragrance of constituent (b) has a molecular weight in the range from 140 through 170 g/mol.

6. The fragrance mixture as claimed in claim 1, wherein constituent (c) consists of two or more different fragrances.

7. The fragrance mixture as claimed in claim 1, wherein the weight ratio of the total amount of fragrances of constituent (c) to the compound of formula (I) is greater than or equal to 99:1.

8. The fragrance mixture as claimed in claim 1, wherein the one or more fragrances of constituent (c) are selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyllinalyl acetate, cedrylmethyl ether, cedrylmethyl ketone, cedryl acetate, (4aR,5R,7aS,9R)-octahydro-2,2,5,8,8,9a-hexamethyl-4H-4a,9-methano azuleno(5,6-d)-1,3-dioxol), 1',1',5',5'-tetramethyl-hexahydro-spiro[1,3-dioxolan-2,8'(5'H)-2H-2,4a]methano-naphthalene, cyclododecylmethyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy-acetate, benzylbenzoate, benzylcinnamate, oxacyclohexa-decan-2-one, 15-hydroxy-pentadecanoic acid lactone, 5-cyclohexadecen-1-one, 3-methyl-cyclopentadecenone, 1,3,4,6,7,8-hexahydro-4,6,6,7,8,8-hexamethyl cyclo-penta[g]-2-benzopyran, 2-[1-(3,3-dimethylcyclohexyl)ethoxy]-2-methyl-, 1-propanoate, 1,4-dioxacycloheptadecane-5,17-dione, 3-methyl-cyclopentadecanone, 8-cyclohexadecen-1-one, 3a,6,6,9a-tetramethyl dodecahydronaphtho[2,1-b]furan, alpha-irone, beta-irone, alpha-n-methylionone, beta-n-methylionone, alpha-isomethylionone, beta-isomethylionone and allyl ionone.

9. The fragrance mixture as claimed in claim 1, wherein constituent (c) comprises methyl dihydrojasmonate.

10. The fragrance mixture as claimed in claim 9, wherein the content of cis-methyl dihydrojasmonate is more than 30 wt percent relative to the total amount of cis- and trans-methyl dihydrojasmonate.

11. A perfumed product containing a sensorially effective amount of a fragrance mixture as claimed in claim 1.

12. The perfumed product as claimed in claim 11, wherein the product is selected from the group consisting of perfume extracts, eaux de partum, eaux de toilette, shaving lotion, eaux de Cologne, pre-shave products, splash Colognes, perfumed tissue wipes, acidic, alkaline and neutral cleansing agents, textile fresheners, ironing aids, liquid detergents, powdered detergents, laundry pretreatment agents, fabric softeners, washing soaps, washing tablets, disinfectants, surface disinfectants, air fresheners, aerosol sprays, waxes and polishes, body-care products, band creams and lotions, foot creams and lotions, depilatory creams and lotions, after-shave creams and lotions, tanning creams and lotions, hair care products, deodorants and antiperspirants, decorative cosmetic products, candles, lamp oils, joss sticks, insecticides, repellents and propellants.

13. The perfumed product as claimed in claim 11 comprising 0.01 to 10 wt percent of the fragrance mixture, relative to the total weight of the perfumed product.

14. A method for producing the fragrance mixture of claim 1 comprising mixing, constituent (a) with constituent (b) and/or (c).

15. The method as claimed in claim 11, wherein the weight ratio of the total amount of fragrances of constituent (h) to the compound of formula (I) is greater than or equal to 99:1, and/or the weight ratio of the total amount of fragrances of constituent (e) to the compound of formula (I) is greater than or equal to 99:1.

16. A method of producing a perfumed product comprising: i) providing a fragrance mixture as claimed in claim 1, ii) providing a further constituents of the perfumed product, and iii) bringing the further constituents of the perfumed product provided in ii) in contact with a sensorially effective amount of the fragrance mixture provided in step i);

wherein the amount of the compound of formula (I) is sufficient to intensify the natural freshness and/or aura of the one or more fragrances of constituents (b) and/or (c) and/or to mask or reduce oily, industrial, and/or metallic notes.

17. A method of intensifying the natural freshness and/or aura and/or for masking or reducing oily, industrial and/or metallic notes of one or more fragrances different from the compound of formula (I) with a floral odor note, comprising mixing the one or more fragrances different from the compound of formula (I) with an amount of the compound of formula (I)

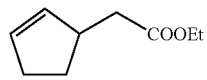 (I)

that is sufficient to intensify the natural freshness and/or aura of the one or more fragrances different from the compound of formula (I) and/or to mask or reduce oily, industrial and/or metallic notes.

18. The method as claimed in claim 17, wherein the one or more fragrances different from the compound of formula (I) are: (b) one or more fragrances selected from the group consisting of alcohols and aldehydes, having a molecular weight of 210 g/mol or less; and/or (c) one or more fragrances selected from the group consisting of ketones, ethers, and esters, having a molecular weight of 190 g/mol to 250 g/mol.

19. The method as claimed in claim 17, wherein the weight ratio of the total amount of the one or more fragrances of constituent (h) to the compound of formula (I) is greater than or equal to 99:1; and/or the weight ratio of the total amount of the one or more fragrances of constituent (c) to the compound of formula (I) is greater than or equal to 99:1.

* * * * *